United States Patent
Liang et al.

(10) Patent No.: US 9,150,463 B2
(45) Date of Patent: Oct. 6, 2015

(54) METHODS AND APPARATUS FOR TREATING A HYDROCARBON STREAM

(71) Applicant: UOP LLC, Des Plaines, IL (US)

(72) Inventors: Wugeng Liang, Elgin, IL (US); Mark G. Riley, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 240 days.

(21) Appl. No.: 13/900,618

(22) Filed: May 23, 2013

(65) Prior Publication Data

US 2013/0324773 A1     Dec. 5, 2013

Related U.S. Application Data

(60) Provisional application No. 61/653,557, filed on May 31, 2012.

(51) Int. Cl.
| | |
|---|---|
| C07C 7/12 | (2006.01) |
| C07C 7/13 | (2006.01) |
| C07C 7/20 | (2006.01) |
| C07C 5/327 | (2006.01) |
| C07C 2/66 | (2006.01) |
| C07C 2/64 | (2006.01) |

(52) U.S. Cl.
CPC . *C07C 2/64* (2013.01); *C07C 5/327* (2013.01); *C07C 7/12* (2013.01)

(58) Field of Classification Search
USPC .......... 585/823, 804, 806, 807, 808, 441, 323
See application file for complete search history.

(56) References Cited

U.S. PATENT DOCUMENTS

| | | |
|---|---|---|
| 4,185,040 A | 1/1980 | Ward |
| 4,774,377 A | 9/1988 | Barger |
| 4,846,962 A | 7/1989 | Yao |
| 4,891,458 A | 1/1990 | Innes |
| 5,030,786 A | 7/1991 | Shamshoum |
| 5,220,099 A | 6/1993 | Schreiner |
| 6,019,887 A | 2/2000 | Ramirez de Agudelo |
| 6,107,535 A | 8/2000 | Rossini |
| 6,297,417 B1 | 10/2001 | Samson |
| 6,756,030 B1 | 6/2004 | Rohde |
| 7,091,390 B2 | 8/2006 | Jan |
| 7,205,448 B2 | 4/2007 | Gajda |
| 7,744,828 B2 | 6/2010 | Schmidt |
| 8,546,630 B2 | 10/2013 | Jan |
| 8,546,631 B2 | 10/2013 | Jan |
| 8,546,632 B2 | 10/2013 | Jan |
| 2009/0326291 A1* | 12/2009 | Jan et al. .................. 585/270 |
| 2013/0323133 A1 | 12/2013 | Liang |
| 2013/0323134 A1 | 12/2013 | Riley |
| 2013/0324774 A1 | 12/2013 | Riley |

FOREIGN PATENT DOCUMENTS

| | | |
|---|---|---|
| WO | 0035836 A1 | 6/2000 |
| WO | 0107383 A1 | 2/2001 |

* cited by examiner

*Primary Examiner* — Thuan D Dang (57) ABSTRACT

Disclosed is a method for treating two or more aromatic feed streams including combining one aromatic feed stream with another aromatic feed stream. The method further includes passing the combined feed stream to a unsaturated aliphatic compound removal zone for removing an unsaturated aliphatic compound therefrom. The method further includes passing the combined aromatic feed stream to a nitrogen removal zone for removing a nitrogen compound therefrom.

5 Claims, 4 Drawing Sheets

METHODS AND APPARATUS FOR TREATING A HYDROCARBON STREAM

CROSS REFERENCE TO RELATED APPLICATION

This application claims priority to U.S. Application No. 61/653,557 which was filed on May 31, 2012.

FIELD OF THE INVENTION

This invention relates to methods and apparatus for treating a hydrocarbon stream. More particularly, this invention relates to methods and apparatus for treating two or more hydrocarbon feed streams that may be combined and may include an aromatic compound to remove nitrogen compounds and unsaturated aliphatic compounds.

BACKGROUND OF THE INVENTION

The alkylation or transalkylation of benzene with a C2 to C20 olefin alkylating agent or a polyaklyl aromatic hydrocarbon transalkylating agent is one of the primary sources for the production of alkyl-benzenes. For example, ethylbenzene is often produced by the alkylation of benzene with ethylene. Ethylbenzene may subsequently be used as a precursor for making styrene by the dehydrogenation of the ethylbenzene. Often, the ethylbenzene and styrene production facilities are integrated in an ethylbenzene-styrene complex so that after the ethylbenzene is produced it is sent to a downstream styrene plant that converts the ethylbenzene into styrene through dehydrogenation. Styrene may in turn be used to produce polystyrene, a widely used plastic, or other products.

In an alkyl-benzene production plant, benzene is fed along with a C2 to C20 olefin alkylating agent or polyalkylaromatic hydrocarbon transalkylating agent to an alkylation and/or transalkylation reactor. Typically, benzene is fed along with ethylene into an alkylation reactor, where alkylation of the benzene and ethylene over an alkylation catalyst forms ethylbenzene. The ethylbenzene product stream typically includes other components as well, such as poly-ethylbenzene. The stream may next be sent to a separation zone where the ethylbenzene is separated from other components in the stream to form a purified ethylbenzene stream.

In an ethylbenzene-styrene complex, the ethylbenzene is next sent to a downstream styrene plant or zone of the complex for conversion of the ethylbenzene to styrene. According to one current process, the ethylbenzene is sent to a dehydrogenation reactor within the styrene plant, where a dehydrogenation reaction occurs to form a mixed stream of styrene, toluene, benzene, and ethylbenzene. The mixed stream is sent to an ethylbenzene-styrene splitter forming separate ethylbenzene and styrene streams. An inhibitor is typically added to the ethylbenzene-styrene splitter to restrict polymerization of the styrene and corrosion within the splitter. In many instances, the inhibitors include nitrogen compounds. The ethylbenzene stream may be sent to an ethylbenzene recycle column where an ethylbenzene recycle stream is separated from benzene and toluene. The ethylbenzene may be recycled back to the dehydrogenation reactor or reactors in order to produce additional styrene. The benzene and toluene are typically sent to a benzene-toluene splitter where the streams are separated and may be sold.

Catalysts for aromatic conversion processes generally comprise zeolitic molecular sieves. Examples include, zeolite beta (U.S. Pat. No. 4,891,458); zeolite Y, zeolite omega and zeolite beta (U.S. Pat. No. 5,030,786); X, Y, L, B, ZSM-5, MCM-22, MCM-36, MCM-49, MCM-56, and Omega crystal types (U.S. Pat. No. 4,185,040); X, Y, ultrastable Y, L, Omega, and mordenite zeolites (U.S. Pat. No. 4,774,377); and UZM-8 zeolites (U.S. Pat. No. 6,756,030 and U.S. Pat. No. 7,091,390). It is known in the art that the benzene stream generated by the styrene zone includes contaminants, such as nitrogen, unsaturated aliphatic compounds, and water such that it has been undesirable to recycle the stream back to the alkylation reactor to produce additional ethylbenzene. These contaminants, even at ppm and ppb levels, can cumulatively act to poison the aromatic conversion catalysts, such as aromatic alkylation catalysts and significantly shorten their useful life. More particularly, nitrogen compounds in the benzene stream, as well as water and dienes or other unsaturated aliphatic compounds, are known to deactivate the alkylation or transalkylation catalyst in the alkylation or transalkylation zone adding additional expense in having to change out or regenerate the catalyst. In addition, due to the contaminants in this stream, the sale of this benzene stream to third parties is generally below the typical market value of benzene A variety of guard beds having clay, zeolite, or resin adsorbents to remove one or more types of nitrogen compounds and/or other contaminants from an aromatic hydrocarbon stream upstream of an aromatic conversion process are known in the art. Examples include: U.S. Pat. No. 7,205,448; U.S. Pat. No. 7,744,828; U.S. Pat. No. 6,297,417; U.S. Pat. No. 5,220,099; WO 00/35836; WO 01/07383; U.S. Pat. No. 4,846,962; U.S. Pat. No. 6,019,887; and U.S. Pat. No. 6,107,535. An acidic molecular sieve H—Y has been utilized to adsorb the nitrogen compounds from the stream. More particularly, several approaches have been proposed for treating the recycle benzene stream from the styrene monomer production zone so that the stream can be used as an additional feed stream to an alkylation zone. Various approaches have also been utilized for treating a fresh benzene feed stream to an ethylbenzene production zone.

Recent attempts, as described in U.S. patent application Ser. Nos. 13/314,796; 13/314,749; and 13/314,842 have focused on removing the olefinic compounds, and in particular dienes such as butadiene or isoprene from a benzene feed stream or a benzene stream exiting the styrene plant prior to directing the stream through a nitrogen compound removal guard bed. In this manner, a large portion of the dienes can be removed from the stream prior to contacting the guard bed catalyst with the stream to restrict the dienes from contacting the guard bed and poisoning the nitrogen adsorbent. With this in mind, these applications propose contacting the benzene or other aromatic stream with adsorbents and/or catalysts including clay, acidic molecular sieves, and/or activated carbon in order to remove at least a portion of the dienes or other C2 to C20 olefin alkylating agent or a poly-alkyl aromatic hydrocarbon transalkylating agents present in a recycle or a fresh feed stream prior to contacting the stream with the nitrogen removal adsorbent to restrict these components from shortening the life of the nitrogen guard bed.

Because the recycle benzene stream from the styrene monomer production zone has different components and concentrations of contaminants than a fresh benzene feed stream provided to an alkylation zone, the recycle benzene stream is treated separately from the fresh benzene streams to remove the contaminants. In other words, because the recycle benzene feed stream requires a higher level of contaminant removal than the fresh benzene stream, and may require different contaminants to be removed, the recycle benzene stream is sent through a recycle stream treatment zone apart from the fresh feed stream treatment zone so that these different concentrations or types of contaminants can be removed.

Increases in crude oil prices have created renewed interest in utilizing available streams for recycle in petrochemical processes. Thus, it is desirable to identify ways to utilize feeds and recycle streams in an effective and economical manner for use in aromatic conversion processes while avoiding the problems associated with the presence of the contaminants in the feeds as discussed above.

DETAILED DESCRIPTION OF THE INVENTION

Hydrocarbon conversion processes, such as, for example, alkylation and/or transalkylation of a benzene feed stream to form ethylbenzene and the dehydrogenation of the ethylbenzene stream to form a styrene monomer stream are well known. Various aspects provided herein provide methods and apparatus for combining two or more hydrocarbon feed streams to a hydrocarbon conversion process and treating the combined hydrocarbon feed stream to remove contaminants therefrom. The two or more hydrocarbon feed streams each includes an aromatic hydrocarbon compound and may include the same aromatic hydrocarbon compound. The two or more hydrocarbon feed streams according to various aspects have different compositions including, different types and/or concentrations of contaminants and may be provided from different sources. For example, one hydrocarbon stream may be a fresh hydrocarbon feed stream and another hydrocarbon feed stream may be a recycle hydrocarbon feed stream. According to various aspects, the contaminants that are removed from the combined hydrocarbon feed stream may include one or more nitrogen compounds and one or more unsaturated aliphatic compounds. Water may also be removed from the combined hydrocarbon feed stream according to various aspects described herein. The treated combined hydrocarbon feed stream has a reduced nitrogen compound and unsaturated aliphatic hydrocarbon content relative to the combined hydrocarbon feed stream.

In accordance with an aspect, the aromatic hydrocarbon compound of the two or more hydrocarbon feed streams may be selected from the group consisting of benzene, toluene, and naphthalene and substituted derivatives thereof, with benzene and its derivatives being preferred aromatic compounds. By one aspect, the two or more feed streams may include the same aromatic hydrocarbon compound, although the concentration of the aromatic hydrocarbon compound may be different. Other hydrocarbon compounds, including aromatic hydrocarbon compounds, may also be present in the two or more feed streams. The aromatic compound may have one or more of the substituents selected from the group consisting of alkyl groups having from 1 to about 20 carbon atoms, hydroxyl groups, and alkoxy groups whose alkyl group also contains from 1 up to 20 carbon atoms. Where the substituent is an alkyl or alkoxy group, a phenyl group can also be substituted on the alkyl chain.

Although unsubstituted and monosubstituted benzenes, toluenes, and naphthalenes, are most often used, polysubstituted aromatics also may be employed. Examples of suitable alkylatable aromatic compounds in addition to those cited above may include anthracene, phenanthrene, biphenyl, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, and so forth. Sources of benzene, toluene, xylene, and or other feed aromatics include product streams from naphtha reforming units, aromatic extraction units, recycle streams from styrene monomer production units, and petrochemical complexes for the producing para-xylene and other aromatics. However, the hydrocarbon feed stream includes at least one aromatic hydrocarbon compound. According to one example, the concentration of the aromatic compound in the hydrocarbon feed stream ranges from about 5 wt % to about 99.9 wt % of the hydrocarbon feed. By another example, the hydrocarbon feed stream comprises between about 50 wt % and about 99.9 wt % aromatics, and may comprise between about 90 wt % and about 99.9 wt % aromatics.

In accordance with one aspect, two or more aromatic hydrocarbon feed streams are combined and the combined aromatic feed stream is sent to a treatment zone. By one aspect one aromatic feed stream to be combined has a different composition than another aromatic feed stream to be combined. For example, one aromatic feed stream may include a fresh aromatic feed stream provided from an upstream process, such as, for example, reforming naphtha to form aromatic compounds and extracting and separating the aromatic compounds to form a fresh aromatic feed stream as is known in the art. A fresh aromatic feed stream may also be provided from other sources. Another aromatic feed stream may be provided from another source, including, for example, a recycle stream from a downstream process. For example, a benzene recycle stream may be provided as a byproduct from a downstream or separate styrene monomer production zone. According to various aspects, because the two or more feed streams are provided from different sources they will have different compositions. While the following description sets forth an example wherein one aromatic feed stream is a fresh aromatic feed stream and the other aromatic feed stream is a recycle aromatic feed stream for ease of explanation, it should be understood that other configurations are contemplated herein wherein one feed stream is provided from one source and another feed stream is provided by another source.

By one aspect, the fresh aromatic feed stream includes a nitrogen compound and may include an organic nitrogen compound. Organic nitrogen compounds typically include basic nitrogen compounds such as indoles, pyridines, quinolines, diethanol amine (DEA), morpholines including N-formyl-morpholine (NFM) and N-methyl-pyrrolidone (NMP). Organic nitrogen compounds may also include weakly basic nitriles, such as acetonitrile, propionitrile, and acrylonitrile. The nitrogen compound in the fresh aromatic feed stream may include a weakly basic nitrogen compound such as a nitrile. Alternatively, or in addition, the fresh aromatic feed stream may include a basic nitrogen compound such as indoles, pyridines, quinolines, diethanol amine (DEA), morpholines including N-formyl-morpholine (NFM) and N-methyl-pyrrolidone (NMP). The fresh aromatic feed stream may include both a weakly basic organic nitrogen compound and a stronger basic organic nitrogen compound.

The fresh aromatic feed stream may also include an unsaturated aliphatic compound, such as, for example an olefinic compound such as a diolefin. The fresh aromatic feed stream may further include water.

By one aspect, the unsaturated aliphatic compound may include unsaturated cyclic hydrocarbons and straight and branched chain olefinic hydrocarbons (olefins) having one or more double bonds. Thus, as used herein the terms "olefins" and "olefinic hydrocarbons" include diolefin compounds. In an example, the unsaturated aliphatic compound is an olefin compound, and the unsaturated aliphatic compound may be a diolefin compound. In another example, the unsaturated aliphatic compound is one or more diolefin compounds having four, five, or six carbon atoms per molecule, i.e. the unsaturated aliphatic compound may be selected from the group of diolefins consisting of C4-C6 acyclic and cyclic diolefins, and mixtures thereof. In yet another example, the diolefin compound is selected from the group consisting of butadienes, pentadienes, methylbutadienes, hexadienes, methylpentadienes, dimethylbutadienes, acetylenes, cyclopentadiene, alkylcyclopentadiene, cyclohexadiene and mixtures thereof.

In an example, the concentration of diolefin compounds in the fresh aromatic feed ranges from about 10 ppb-wt to about 100 ppm-wt of the fresh aromatic feed; and the concentration of diolefin compounds may range from about 100 ppb-wt to about 1000 ppm-wt of the fresh aromatic feed. The fresh aromatic feed stream may comprise other olefins such as mono-olefins. Typically, the overall concentration of all olefins in the fresh aromatic feed stream will be no more than 1 wt-% olefins.

By one aspect the fresh aromatic feed stream has a basic nitrogen compound content ranging from about 10 ppb-wt to about 100 ppm-wt. In another example, the concentration of basic nitrogen compounds in the fresh aromatic feed ranges from about 100 ppb-wt to about 10 ppm-wt of the fresh aromatic feed. In another example the concentration of weakly basic nitrogen compounds in fresh aromatic feed may range from about 10 ppb-wt to about 1 ppm-wt of the fresh aromatic feed and in another example between about 100 ppb-wt to about 1 ppm-wt. In yet another example, the overall concentration of all organic nitrogen compounds in the fresh aromatic feed ranges from about 10 ppb-wt to about 100 ppm-wt.

In accordance with one aspect, the fresh aromatic feed stream contains water. In an example, the concentration of water in the fresh aromatic feed stream ranges from about 1 to about 5,000 ppm-wt of the fresh aromatic feed stream. In accordance with another example, the concentration of water in the fresh aromatic feed stream ranges from about 1 to about 1,000 ppm-wt. The fresh aromatic feed stream may also contain oxygenates in addition to water such as, for example, alcohols and ketones that may be removed with the water components from the fresh aromatic feed stream.

In an example, the fresh feed stream includes an aromatic compound comprising benzene, a nitrogen compound comprising an organic nitrogen compound, and an unsaturated aliphatic compound comprising an olefin compound. In another example, the fresh feed stream includes an aromatic compound comprising benzene, a nitrogen compound comprising a basic organic nitrogen compound, and an unsaturated aliphatic compound comprising an olefin compound having four to six carbon atoms per molecule. In another example, the fresh feed stream includes an aromatic compound comprising benzene, a nitrogen compound comprising a basic organic nitrogen compound, and an unsaturated aliphatic compound comprising a diolefin compound.

By one aspect, the recycle aromatic feed stream also includes a nitrogen compound. The nitrogen compound in the recycle aromatic feed stream may include a weakly basic nitrogen compound, such as organic nitrogen compound as discussed above, including a nitrile. The recycle aromatic feed stream nitrogen compound may be the same as or may be different from the nitrogen compound in the fresh aromatic feed stream. In addition, or alternatively, the recycle aromatic feed stream nitrogen compound may be present at a different concentration than the nitrogen compound in the fresh aromatic feed stream. For example, where the one aromatic feed stream includes a nitrile or other weakly basic nitrogen component, the recycle aromatic feed stream may include a higher concentration of the nitrile or other weakly basic nitrogen component. Similarly, where the one aromatic feed stream includes a basic organic nitrogen compound, the recycle aromatic feed stream may include a weakly basic organic nitrogen compound. The recycle aromatic feed stream may also include an unsaturated aliphatic compound, such as, for example, those described above with regard to the one aromatic feed stream. The unsaturated aliphatic compound in the recycle aromatic feed stream may include the same or a different unsaturated aliphatic compound than the fresh aromatic feed stream. The concentration of the unsaturated aliphatic compound in the recycle aromatic feed stream may also be different than the concentration in the fresh aromatic feed stream. The recycle aromatic feed stream may further include water at the same or a different concentration than in the one aromatic feed stream.

According to one aspect, the nitrogen compound in the recycle aromatic feed stream may result from adding an inhibitor or a retardant in an upstream process or downstream process where a process stream is recycled back upstream. For ease of explanation, inhibitors and retardants will collectively be referred to as "inhibitors" from here forward. Adding various nitrogen compound containing inhibitors to a stream during certain processes has been found to inhibit polymerization of a component in the stream and/or reduce corrosion of equipment within a processing unit. For example, as illustrated in FIG. 3, which is addressed again further below, an inhibitor may be added to a styrene monomer production zone 205 of an ethylbenzene-styrene complex in order to inhibit polymerization of a styrene monomer within a styrene stream during separation of a styrene product from other components in the styrene stream, in for example, separation zone 255. The inhibitor may also act to reduce corrosion within the vessels used to carry out these processes. In this example, when a benzene stream is recycled from the styrene monomer production zone 205 to provide at least a portion of a hydrocarbon feed stream comprising benzene, the recycle benzene stream may contain residual nitrogen compounds from the upstream addition of the inhibitor. The hydrocarbon feed stream nitrogen compound may be in the same or a different form than the inhibitor nitrogen compound, due to, for example, a reaction or conversion of the inhibitor nitrogen compound.

Chemical compositions of proprietary inhibitors in commercial use are not widely known, however, certain typical characteristics of such inhibitors are generally understood. U.S. Pat. No. 7,276,636, which is incorporated herein by reference, provides a description of the use of inhibitors, general characteristics of inhibitors, and examples of inhibitors that may be used in commercial processes in Col. 3, line 41 through col. 4, line 65. These inhibitors, as well as others, may introduce the nitrogen compounds present in the hydrocarbon feed stream. Some specific, non-limiting examples of nitrogen compounds that may be found in inhibitors include dinitrophenols, 2-sec-butyl-4,6-dinitrophenol, dialkylhydroxylamines, and nitroxides as well as those described in U.S. Pat. No. 7,276,636.

In an example, the concentration of diolefin compounds in the recycle aromatic feed stream ranges from about 30 ppb-wt to about 3000 ppm-wt of the recycle aromatic feed stream; and the concentration of diolefin compounds may range from about 50 ppb-wt to about 2000 ppm-wt of the recycle aromatic feed stream. The recycle aromatic feed stream stream may comprise other olefins such as mono-olefins. Typically, the overall concentration of all olefins in the recycle aromatic feed stream will be no more than 1.0 wt-% olefins.

In one example, the recycle aromatic feed stream stream has a nitrogen component content ranging from about 1 ppm-wt to about 10 ppm-wt. In another example, the concentration of organic nitrogen compounds in the recycle aromatic feed stream ranges from about 30 ppb-wt (parts per billion by weight) to about 1 mole % of the recycle aromatic feed stream; the concentration of organic nitrogen compounds may range from about 30 ppb-wt to about 100 ppm-wt (parts per million by weight) of the recycle aromatic feed stream. In yet another example, the concentration of weakly basic organic nitrogen compounds such as nitriles in the recycle aromatic feed stream ranges from about 100 ppb-wt to about 100 ppm-wt of the recycle aromatic feed stream.

In accordance with one aspect, the recycle aromatic feed stream contains water. In an example, the concentration of water in the recycle aromatic feed stream ranges from about 10 to about 5,000 ppm-wt. In accordance with another example, the concentration of water in the recycle aromatic feed stream ranges from about 10 to about 1,000 ppm-wt. The recycle aromatic feed stream may also contain oxygenates in addition to water such as, for example, alcohols and ketones that may be removed with the water components from the recycle aromatic feed stream.

In an example, the recycle feed stream includes an aromatic compound comprising benzene, a nitrogen compound comprising an organic nitrogen compound, and an unsaturated aliphatic compound comprising an olefin compound. In another example, the recycle feed stream includes an aromatic compound comprising benzene, a nitrogen compound comprising a basic organic nitrogen compound, and an unsaturated aliphatic compound comprising an olefin compound having four to six carbon atoms per molecule. In another example, the recycle feed stream includes an aromatic compound comprising benzene, a nitrogen compound comprising a basic organic nitrogen compound, and an unsaturated aliphatic compound comprising a diolefin compound.

According to one aspect, the volumetric flow rate of the fresh aromatic feed stream is greater than the volumetric flow rate of the recycle aromatic feed stream such that the combined aromatic feed stream includes a larger volume of the fresh aromatic feed stream. In one example the volumetric flow rate of the fresh aromatic feed stream is between about 10 times and about 100 times greater than the volumetric flow rate of the recycle aromatic feed stream. In another example, the volumetric flow rate of the fresh aromatic feed stream is between about 30 times and about 100 times greater than the volumetric flow rate of the recycle aromatic feed stream. In this regard, the combined aromatic feed stream comprises between about 90% and about 99% of the fresh aromatic feed stream and between about 1% and about 10% of the recycle aromatic feed stream.

By one aspect, the fresh and recycle aromatic feed streams are combined to form a combined feed stream. The combined aromatic feed stream is then passed to a treatment zone to remove contaminants from the combined hydrocarbon feed stream. Surprisingly, it has been discovered that a common treatment zone is effective for removing an acceptable level of the nitrogen compound and unsaturated aliphatic compound contaminants from the combined aromatic feed stream without quickly deactivating materials used to remove the contaminants in the treatment zone, even though the fresh and recycle aromatic feed streams that formed the combined aromatic feed stream had different compositions. It should be appreciated that while the hydrocarbon conversion processes and apparatus are described herein in terms of combining one aromatic feed stream with another aromatic feed stream, it may also be carried out in systems where more than two hydrocarbon feed streams are utilized, and where more than two hydrocarbon feed streams are present the additional hydrocarbon streams may be combined with the first and second hydrocarbon feed streams.

Figure 1:
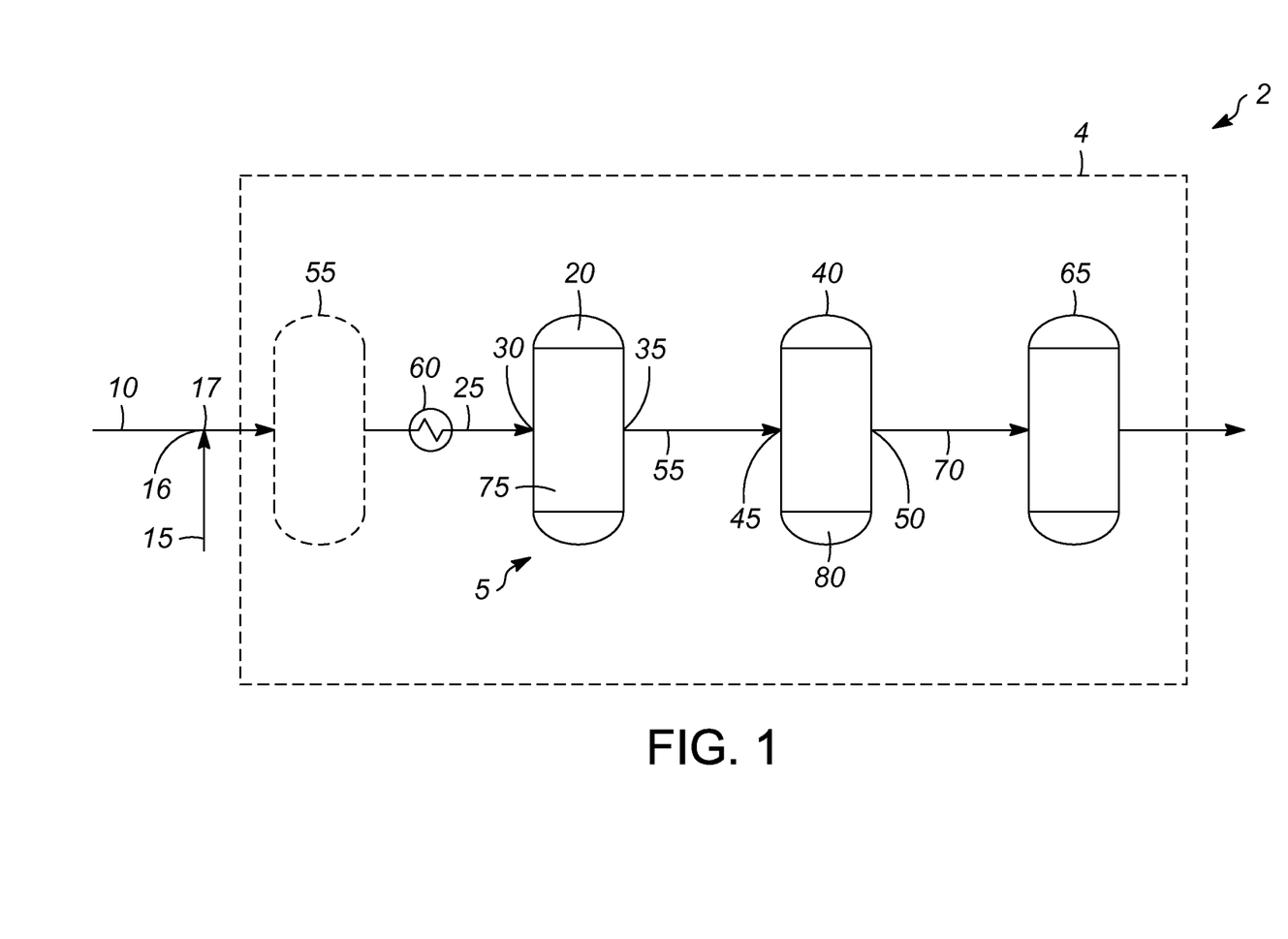
FIG. 1 is a flow diagram of a hydrocarbon feed stream treatment zone in accordance with various embodiments.

Turning to FIG. 1, an apparatus 2 and process for treating a combined aromatic feed stream is provided. The apparatus 2 includes a combined treatment zone 4 for removing one or more compounds from the feed stream. The treatment zone includes one or more vessels 5 for treating the combined aromatic feed stream. By one aspect, one aromatic feed stream, for example a fresh aromatic feed stream, is provided via line or conduit 10 to the combined treatment zone. Another aromatic feed stream, for example a recycle aromatic feed stream, is provided via line or conduit 15 to the combined treatment zone 4. The fresh aromatic feed stream and the recycle aromatic feed stream are combined before entering the treatment zone via a juncture between the fresh feed line 10 and the recycle feed line 15. In one example, the juncture includes a coupling 17 that is provided between line 10 and line 15 upstream of or within the treatment zone 4 for combining the fresh and recycle aromatic feed streams, as illustrated in FIG. 1. In another example, the juncture includes a vessel 5 within the treatment zone 4 and the fresh and recycle aromatic feed streams are combined in the vessel 5.

By one aspect, the treatment zone includes an unsaturated aliphatic removal zone 20 for removing one or more unsaturated aliphatic compounds from the combined aromatic feed stream. The unsaturated aliphatic compound removal zone 20 is in fluid communication with the juncture 16 by line 25 and includes an unsaturated aliphatic compound removal zone inlet 30 and an unsaturated aliphatic compound removal zone outlet 35. The unsaturated aliphatic compound removal zone 20 removes at least one unsaturated aliphatic compound from the feed stream to provide a reduced unsaturated aliphatic compound feed stream that has a lower concentration of the one or more unsaturated aliphatic compounds than the combined aromatic feed stream entering the unsaturated aliphatic removal zone 20. By one aspect, the unsaturated aliphatic compound removal zone includes an unsaturated aliphatic compound selective material that preferentially adsorbs or converts the unsaturated aliphatic compounds in the combined aromatic feed stream over one or more other components in the feed stream in order to remove them therefrom. The unsaturated aliphatic compound removal zone 20 may also remove a portion of one or more organic nitrogen compounds from the combined aromatic feed stream as further described below. The unsaturated aliphatic compound removal selective material may be particularly effective at removing basic organic nitrogen compounds from the combined aromatic feed stream which may be present from the fresh aromatic feed stream. Beneficially, the unsaturated aliphatic removal zone 20 removes one or more unsaturated aliphatic compounds from the feed stream and may also remove a portion of one or more nitrogen compounds from the feed stream. This can advantageously reduce the deactivation that occurs of a downstream nitrogen removal adsorbent.

By one aspect, the feed stream treatment zone 4 also includes a nitrogen removal zone 40, having a nitrogen removal zone inlet 45 and a nitrogen removal zone outlet 50. The reduced unsaturated aliphatic compound feed stream is provided to the nitrogen removal zone 40 via the line 55, which provides fluid communication between the unsaturated aliphatic compound removal zone 20 and the nitrogen removal zone 40. The nitrogen removal zone 40 removes one or more nitrogen compounds from the feed stream to provide a reduced nitrogen aromatic feed stream that has a lower nitrogen concentration than the reduced water feed stream entering the nitrogen removal zone 40 via the inlet 45. By one aspect, the nitrogen removal zone 40 includes a nitrogen selective adsorbent that contacts the feed stream and preferentially adsorbs nitrogen over one or more other components in the feed stream for removing the nitrogen compound from the feed stream. A reduced nitrogen feed stream exits the nitrogen removal zone 40 via the outlet 50.

According to another aspect, the treatment zone 4 may include a light ends separation device 55, for example a fractionation column, for separating low molecular weight compounds from the combined aromatic feed stream. For example, where the aromatic compound includes benzene, the separation device 55 may separate at least one low molecular weight compound, including one or more compounds selected from the group consisting of ethane, ethylene, propane, propylene, butane, butenes and butadiene, and other low molecular weight compounds as is understood by those of ordinary skill in the art. The light ends separation device 55 may be positioned upstream of one or both of the unsaturated aliphatic compound removal zone 20 and the nitrogen removal zone 40. As illustrated in FIG. 1, the light ends separation device 55 may be positioned between the juncture 16 and the unsaturated aliphatic compound removal zone 20 to removal the low molecular weight compounds before the combined aromatic feed stream is passed to the unsaturated aliphatic compound removal zone and may be in fluid communication with both the juncture 16 and the unsaturated aliphatic compound removal zone 20.

By one aspect, one or more heat exchangers 60 may be included in the treatment zone 4 and configured to heat the combined aromatic feed stream to a contacting temperature. The heat exchanger 60 may be positioned upstream of the unsaturated aliphatic compound removal zone 20 to heat the combined feed stream to a contacting temperature prior to the feed stream entering the unsaturated aliphatic compound removal zone 20. Alternatively or additionally, a heat exchanger may be positioned between the unsaturated aliphatic compound removal zone 20 and the nitrogen removal zone 40 for heating the combined feed stream to a contacting temperature prior to the combined feed stream entering the nitrogen removal zone 40.

Figure 2:
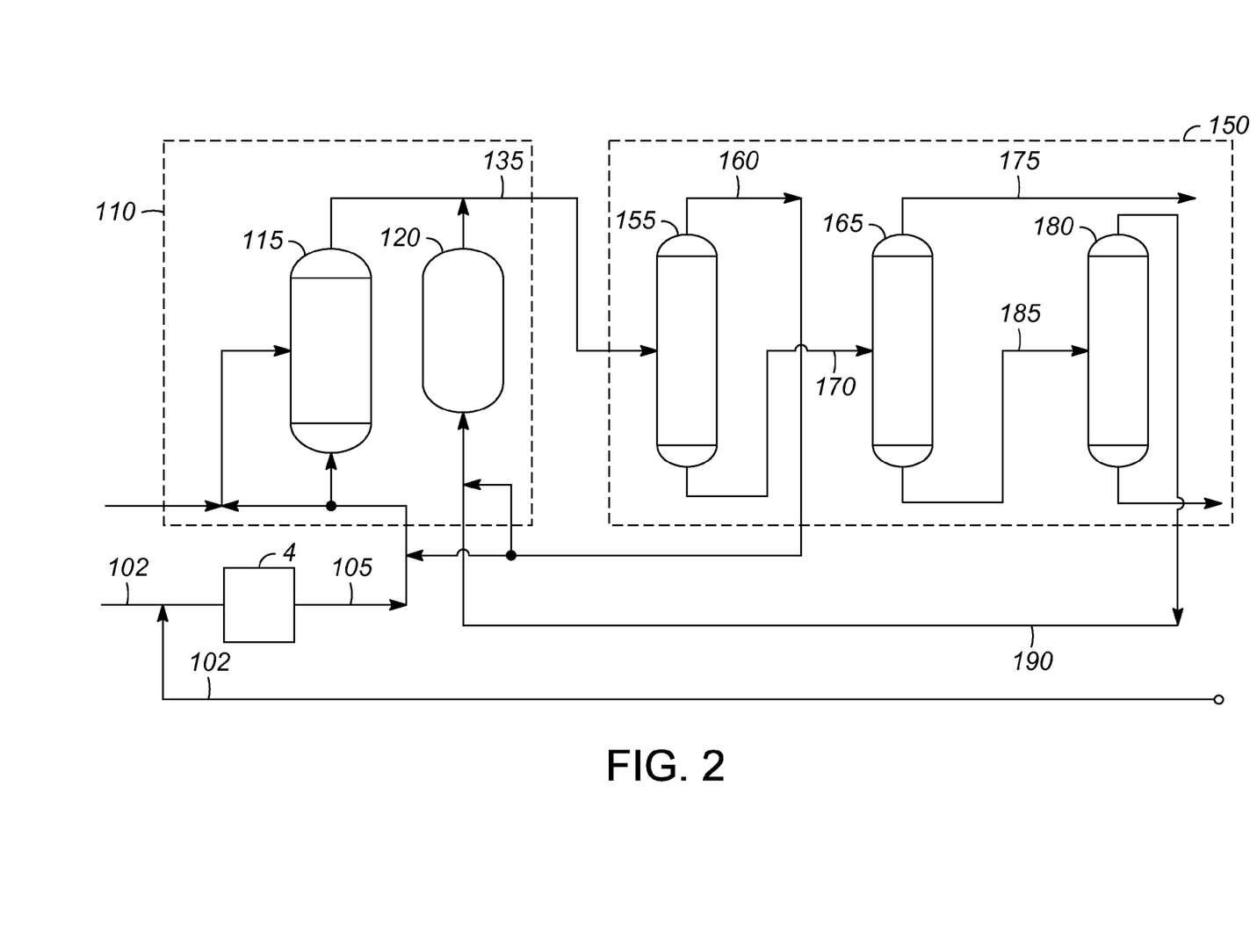
FIG. 2 is a flow diagram of an alkylation facility that includes a hydrocarbon feed stream treatment zone in accordance with various embodiments.

According to another aspect, an aromatic compound separation device 65, for example a fractionation column, may be provided to provide a concentrated aromatic hydrocarbon feed stream. The aromatic compound separation device 65 may be provided for removing some of the water from the stream entering the separation device 65. The separation device 65 may also remove other components from the stream. While FIGS. 1 and 2 illustrate a separate aromatic separation device 65 for ease of explanation, it should be understood that the aromatic separation device may include one or more other separation devices within a larger system. For example, in the ethylbenzene production facility illustrated in FIG. 2, the aromatic compound separation device may include the benzene fractionation column 155. In this regard, a stream exiting the nitrogen removal zone 40 may be sent to the benzene fractionation column 155 or other separation device in a hydrocarbon conversion process for removing water and/or other components to form a concentrated aromatic feed stream. The concentrated aromatic feed stream may then be sent to an alkylation or transalkylation zone, for example via line 160 or another line. Similarly, a water removal zone may be provided for removing water and may include a water removal material for removing water from the stream. For example a water selective adsorbent may be provided in a water removal zone for contacting the nitrogen reduced aromatic feed stream and removing at least a portion of the water from the stream.

Turning to more of the particulars, as described previously, the unsaturated aliphatic compound removal zone 20 includes an unsaturated aliphatic compound removal material. The unsaturated aliphatic compound removal material may include an adsorbent for contacting the combined aromatic feed stream and preferentially adsorbing one or more unsaturated aliphatic compounds from the combined aromatic feed stream over one or more other components in the feed stream, including an aromatic compound. The unsaturated aliphatic compound removal material may also include a catalyst for catalyzing a reaction to convert one or more unsaturated aliphatic compounds in the combined aromatic feed stream to another compound in order to remove the unsaturated aliphatic compounds. The unsaturated aliphatic compound removal material may also include one or more other materials configured for contacting the combined aromatic feed stream and removing one or more unsaturated aliphatic compounds from the stream.

In one example, the unsaturated aliphatic compound removal material includes clay. Suitable clays include for example, beidellite, hectorite, laponite, montmorillonite, nontonite, saponite, bentonite, and mixtures thereof. Examples of suitable, commercially available, clay adsorbents include F-Series adsorbents available from BASF and TONSIL adsorbents such as CO 630 G and CO 616 GS available from Sud-Chemie. In an embodiment, the clay adsorbent is an acid activated bentonite and/or montmorillonite clay. In another example, the unsaturated aliphatic compound removal material includes activated carbon. Activated carbon is well known in the art and may be derived from various sources including petroleum coke, coal, wood, and shells, such as coconut shells, using carbonization and/or activation process steps. Activation may be accomplished, e.g. by thermal treatment under an atmosphere of $CO_2$, $H_2O$ and mixtures thereof, by chemical treating steps, and combinations thereof. Suitable activated carbon is commercially available and may be obtained for example from Calgon.

In yet another example, the unsaturated aliphatic removal material includes an acidic molecular sieve to adsorb or otherwise remove the unsaturated aliphatic compound from the hydrocarbon feed stream. Suitable acidic molecular sieves include the various forms of silicoaluminophosphates, and aluminophosphates disclosed in U.S. Pat. No. 4,440,871; U.S. Pat. No. 4,310,440 and U.S. Pat. No. 4,567,029 as well as zeolitic molecular sieves, which are incorporated herein by reference. As used herein, the term "molecular sieve" is defined as a class of adsorptive desiccants which are highly crystalline in nature, with crystallographically defined microporosity or channels, distinct from materials such as gamma-alumina Preferred types of molecular sieves within this class of crystalline adsorbents are aluminosilicate materials commonly known as zeolites. The term "zeolite" in general refers to a group of naturally occurring and synthetic hydrated metal aluminosilicates, many of which are crystalline in structure. Zeolitic molecular sieves in the calcined form may be represented by the general formula:

$$Me_{2/n}O:Al_2O_3:xSiO_2:yH_2O$$

where Me is a cation, x has a value from about 2 to infinity, n is the cation valence and y has a value of from about 2 to 10. Typical well-known zeolites that may be used include chabazite, also referred to as Zeolite D, clinoptilolite, erionite, faujasite, Zeolite Beta (BEA), Zeolite Omega, Zeolite X, Zeolite Y, MFI zeolite, Zeolite MCM-22 (MWW), ferrierite, mordenite, Zeolite A, Zeolite P, and UZM-8 type zeolites referenced below. Detailed descriptions of some of the above-identified zeolites may be found in D. W. Breck, ZEOLITE MOLECULAR SIEVES, John Wiley and Sons, New York, 1974.

Significant differences exist between the various synthetic and natural materials in chemical composition, crystal structure and physical properties such as X-ray powder diffraction patterns. The molecular sieves occur as agglomerates of fine crystals or are synthesized as fine powders and are preferably tableted or pelletized for large-scale adsorption uses. Pelletizing methods are known which are very satisfactory because the sorptive character of the molecular sieve, both with regard to selectivity and capacity, remains essentially unchanged. In an embodiment, the adsorbent includes a Zeolite Y and/or Zeolite X having an alumina or silica binder and/or a beta zeolite having an alumina or silica binder. In an embodiment, the acidic molecular sieve is Zeolite Y.

In an embodiment, the molecular sieve will usually be used in combination with a refractory inorganic oxide binder. Binders may include either alumina or silica with the former preferred and gamma-alumina, eta-aluminum and mixtures thereof being particularly preferred. The molecular sieve may be present in a range of from 5 to 99 wt-% of the adsorbent and the refractory inorganic oxide may be present in a range of from 1 to 95 wt-%. In an embodiment, the molecular sieve will be present in an amount of at least 50 wt-% of the adsorbent and more preferably in an amount of at least 70 wt-% of the adsorbent.

The molecular sieve according to this example is acidic. Using silicon to aluminum ratio as a gauge for acidity level, the silicon to aluminum ratio should be no more than 100 in an embodiment and no more than 25 in a further embodiment. Cations on the molecular sieve are not desirable. Hence, acid washing may be desirable to remove alkali metals such as sodium in the case of Zeolite Y and Beta Zeolite to reveal more acid sites, thereby increasing the adsorptive capacity. Aluminum migrating out of the framework into the binder should also be avoided because it reduces acidity. Incorporation of some level of cations such as alkali earth and rare earth elements into Zeolite X or Y will improve the thermal and hydrothermal stability of the framework aluminum, minimizing the amount of framework aluminum migrating out of the framework, and may impart sites of varying acidic strength. The level of incorporation of the cations should be balanced to improve overall acidity and/or hydrothermal stability, without inhibiting adsorption performance that may result at higher cation incorporation levels. The molecular sieve adsorbent of the present invention may have the same composition as the alkylation catalyst in a downstream reactor, such as an alkylation or transalkylation unit. However, when the alkylation catalyst is more expensive than the molecular sieve adsorbent, the composition of the alkylation catalyst and the molecular sieve are preferably different.

The combined aromatic feed stream to be treated is contacted with the unsaturated aliphatic compound removal material at contacting conditions to remove one or more unsaturated aliphatic compounds and produce a reduced unsaturated aliphatic compound aromatic feed stream. The unsaturated aliphatic compounds may be removed from the hydrocarbon stream by various mechanisms such as adsorption, reaction, and reactive adsorption with the unsaturated aliphatic compound removal material. The reduced unsaturated aliphatic compound stream has a lower unsaturated aliphatic compound content relative to the unsaturated aliphatic compound content of the combined aromatic feed stream.

According to one aspect, the unsaturated aliphatic compound removal material also removes at least a portion of the organic nitrogen compounds from the feed stream. The unsaturated aliphatic compound removal material may remove at least a portion of the weakly basic organic nitrogen compounds present from the recycle aromatic feed stream. The unsaturated aliphatic compound removal material may be particularly effective for removing a portion of the basic organic nitrogen compounds present from the fresh aromatic feed stream. Without intending to be bound by theory, it is believed that by removing at least a portion of the unsaturated aliphatic compounds from the aromatic feed stream, the downstream nitrogen removal adsorbent will not be contaminated with these components, increasing useful life of the nitrogen removal adsorbent. Similarly, it is believed that by removing at least a portion of the basic organic nitrogen compounds from the aromatic feed stream prior to contacting the nitrogen removal adsorbent results in the nitrogen removal adsorbent not becoming contaminated with these compounds, increasing the life of the nitrogen removal adsorbent. Remaining nitrogen compounds in the combined aromatic feed stream may then be removed by contacting the downstream nitrogen removal adsorbent.

The contacting conditions include a temperature of at least about 25° C. and the presence of water in an amount of at least about 50 ppm relative to the hydrocarbon feed stream on a weight basis. Water may be present in an amount equal to or beyond the saturation point of the hydrocarbon feed stream at the contacting conditions. In an embodiment, water is present in an amount of at least about 250 ppm relative to the hydrocarbon feed stream on a weight basis. In another embodiment, water is present in an amount ranging from about 300 ppm to about 800 ppm relative to the hydrocarbon feed stream on a weight basis. The amount of water during contacting may be controlled in any suitable manner. For example, the water content of the hydrocarbon feed may be monitored and controlled by drying and/or adding water or water generating compounds to the feed stream. Water or water generating compounds may be introduced as a separate stream to the contacting step, and the feed stream may be dried to a consistent water level while water or water generating compounds are added to obtain the desired content. In an example, the contacting temperature ranges from about 25° C. to about 300° C. and the contacting temperature may range from about 45° C. to about 250° C. In another example, the contacting temperature ranges from about 75° C. to about 225° C.; and the contacting temperature may range from about 125° C. to about 300° C.

In an example, the amount of water is at least about 50 ppm relative to the hydrocarbon feed stream on a weight basis. In another example, the amount of water is at least about 250 ppm relative to the hydrocarbon feed stream on a weight basis. In another example, the amount of water equals or exceeds the saturation point of the hydrocarbon feed stream at the contacting conditions. In a further example, the amount of water ranges from about 300 ppm to about 800 ppm relative to the hydrocarbon feed stream on a weight basis. For each of these examples, the contacting temperatures may include the ranges described in the immediately preceding paragraph. Optionally, the contacting conditions may further include a pressure from about 34.5 kPa(g) to about 4136.9 kPa(g). In an example, the contacting is conducted with the feed in the liquid phase or partial liquid phase. Gas phase contacting may also be used.

Bromine Index is commonly used to assess the unsaturated aliphatic compound content, including olefins and diolefins, of hydrocarbon mixtures. (It should be noted that the terms "diolefins" and "dienes" are used interchangeably herein) In one example, the unsaturated aliphatic compound removal zone 50 reduces the diolefin concentration in the hydrocarbon feed stream such that Bromine Index is reduced by at least 50%. The Bromine Index is reduced by at least about 70% in another example; at least about 90% in another example, and at least about 95 wt % in yet another example. As used herein the Bromine Index of the hydrocarbon streams or mixtures is determined using method UOP304. Unless otherwise noted, the analytical methods used herein such as UOP304 are available from ASTM International, 100 Barr Harbor Drive, West Conshohocken, Pa., USA.

The nitrogen removal zone 40 produces a nitrogen reduced aromatic feed stream that may exit the outlet 50 via line or conduit 70 having a lower concentration of the nitrogen compound relative to the treated hydrocarbon stream. As discussed above, various methods are well known in the art to remove nitrogen compounds from aromatic hydrocarbon streams. See, for example, U.S. Pat. No. 7,205,448; U.S. Pat. No. 7,744,828; U.S. Pat. No. 6,297,417; each of which is herein incorporated by reference in its entirety. In brief, the treated hydrocarbon stream is introduced to the nitrogen removal zone 40 which includes at least one adsorbent effective to remove nitrogen. Suitable adsorbents include clays, resins, and zeolites. Typically, the clay and zeolite adsorbents are acidic. The nitrogen removal zone 40 may comprise two adsorbents such as a clay or resin adsorbent being located upstream of a zeolite adsorbent so the treated hydrocarbon stream contacts the clay or resin adsorbent first to produce an intermediate stream which then contacts the zeolite adsorbent. Different operating conditions including temperatures and the amount of water present have been disclosed for different adsorbents and the use of multiple adsorbents in the nitrogen removal zone 40.

According to one aspect, the combined aromatic feed stream is contacted with an adsorbent comprising an acidic molecular sieve at nitrogen removal conditions to produce the alkylation substrate stream having a reduced nitrogen content. In an example the molecular sieve is a zeolite. Well known zeolites that may be used include chabazite, also referred to as Zeolite D, clinoptilolite, erionite, faujasite, Zeolite Beta (BEA), Zeolite Omega, Zeolite X, Zeolite Y, MFI zeolite, Zeolite MCM-22 (MWW), ferrierite, mordenite, Zeolite A, Zeolite P, and UZM-8 type zeolites referenced below. In an embodiment, the nitrogen removal conditions comprise a temperature ranging from at least about 120° C. to about 300° C., and the presence of water in an amount ranging from about 20 ppm to about 500 ppm relative to the treated hydrocarbon stream on a weight basis.

By one aspect, the treatment zone 4 includes both of the unsaturated aliphatic compound removal zone 20 and the nitrogen removal zone 40. According to one aspect, the unsaturated aliphatic compound removal zone 20 and the nitrogen removal zone 40 are provided in series, such that the combined aromatic feed stream is treated by sequentially passing the combined aromatic feed stream through the unsaturated aliphatic compound removal zone 20 and the nitrogen removal zone 40.

The unsaturated aliphatic compound removal zone 50 may include an unsaturated aliphatic compound removal vessel 75 as illustrated in FIG. 1 for holding the unsaturated aliphatic compound selective material, such that the hydrocarbon feed stream enters the unsaturated aliphatic compound removal vessel 75 through the inlet 30 to contact the unsaturated aliphatic compound selective material and exit through the outlet 35. The inlet 30 and outlet 35 may be an inlet and outlet to and from the vessel 52. The unsaturated aliphatic compound removal zone 20 may also be combined into a single vessel with the nitrogen removal zone 40. Internal structures or equipment within a single vessel may separate the different zones. In this regard, the inlet and/or outlet 30 and 35 may be an inlet and/or outlet to or from a particular region of a larger vessel that contains the aliphatic compound removal zone 20 and one or more of the other zones.

The nitrogen removal zone 40 may include a nitrogen removal vessel 80 as illustrated in FIG. 1 for holding the nitrogen selective adsorbent, such that the hydrocarbon feed stream enters the nitrogen removal vessel 80 through the inlet 45 to contact the nitrogen selective adsorbent and exit through the outlet 50. In this approach, the inlet 45 and outlet 50 may be an inlet and outlet to the vessel 80. The nitrogen removal zone 40 may also be combined into a single vessel with the unsaturated aliphatic compound removal zone 20. Internal structures or equipment within a single vessel may separate the different zones. In this regard, the inlet and/or outlet may be an inlet and/or outlet to or from a particular region of a larger vessel that contains the nitrogen removal zone 40 and one or more of the other zones.

In one example, at least about 50% of the nitrogen is removed from the hydrocarbon feed stream, as measured, for example by a nitrogen chemiluminescence method, ASTM D4629. In another example, between about 70% and about 99.99% of the nitrogen is removed from the hydrocarbon feed stream as it contacts the nitrogen selective molecular sieve, and in another example between about 90% and about 99.99%. According to one aspect, the hydrocarbon feed stream to the nitrogen removal zone 30 includes between about 0.03 and about 10 ppm nitrogen.

Turning to FIG. 2, by one aspect, the hydrocarbon stream treatment zone 4 is provided for treating a combined benzene feed stream to an alkylation zone 110. According to various aspects, a fresh benzene feed stream is provided along line 102 and a recycle benzene stream is provided along line 103. The fresh benzene feed stream includes benzene, and may include water, a nitrogen compound, and an unsaturated aliphatic compound as mentioned previously. The recycle benzene feed stream includes benzene, and may include the same or a different nitrogen compound, the same or a different unsaturated aliphatic compound, and may also include water. The concentrations of these components may also be different. The fresh benzene feed stream and the recycle benzene feed stream are combined via a junction 16 between line 102 and line 103. As discussed above, the junction 16 may be a coupling or it may be a vessel where the streams are combined. The combined benzene feed stream is then treated in the treatment zone 4. After the benzene containing feed stream is treated in the hydrocarbon treatment zone 4 to remove at least a portion of a nitrogen compound and an unsaturated aliphatic compound as described above with regard to FIG. 1, the treated feed stream is passed along conduit or line 105 to the alkylation zone 110. By another aspect, as described previously, the treated stream may be passed to a separation device, for example benzene fractionation column 155, and returned to the alkylation zone, for example by line 160. By one aspect, FIG. 2 illustrates that the alkylation zone 110 includes both an alkylation reactor 115 and a transalkylation reactor 120. However, the alkylation zone 110 may not include either the alkylation reactor 115 or the transalkylation reactor 120 and may include more than one alkylation reactor 115 and/or transalkylation reactor 120. FIG. 2 illustrates that the treated hydrocarbon feed stream is combined with another feed stream and passed into the alkylation reactor 115. However, it should be understood that the treated hydrocarbon feed stream can be combined with one or more other streams to pass into the alkylation reactor 115 or the transalkylation reactor 120 or be passed directly into the alkylation reactor 115 or transalkylation reactor 120. It should also be understood that one or more other streams may be combined with the fresh benzene feed stream and/or the recycle benzene feed stream prior to passing the combined feed stream to the treatment zone 4.

In one aspect, the treated hydrocarbon stream is passed via line 105 to one or both of the alkylation reactor 115 and transalkylation reactor 120. Another feed stream 125 may be introduced to the alkylation zone 110 and combined with the treated hydrocarbon feed stream or passed separately to one or both of the alkylation reactor 115 and/or transalkylation reactor 120. In addition, or alternatively, one or more additional streams may be passed to the alkylation zone 110. An alkylating agent may be introduced into an alkylation reactor 115 and contacted with the treated hydrocarbon stream and an alkylation catalyst to produce an alkylated benzene product which is sent downstream via line 135. For example, ethylene may be introduced through line 130 to the alkylation reactor 115 to contact the alkylation catalyst in the presence of a treated benzene feed stream to produce an ethylbenzene stream.

In the selective alkylation of an aromatics alkylation substrate by an olefinic alkylating agent as catalyzed by an acidic catalyst, the olefins may contain from 2 up to at least 20 carbon atoms, and may be branched or linear olefins, either terminal or internal olefins. Thus, the specific nature of the olefin is not particularly important. Among the lower olefins, ethylene and propylene are the most important representatives. An olefinic feed stream may be introduced via line 130 and may include for example an alkylating agent of ethylene and/or propylene. Alkylating agents may also be provided by alkyl constituents of a polyalkylbenzene in a transalkylation reactor 120. Diethylbenzene, triethylbenzene and diisopropylbenzene are prominent examples of polyalkylbenzenes that can provide such alkylating agents.

A wide variety of catalysts can be used in the alkylation zone 110. The preferred catalyst for use in this invention is a zeolitic catalyst. The catalyst of this invention will usually be used in combination with a refractory inorganic oxide binder. Preferred binders are alumina or silica. Suitable zeolites include zeolite beta described in U.S. Pat. No. 5,723,710, ZSM-5, PSH-3, MCM-22, MCM-36, MCM-49, MCM-56, type Y zeolite, and UZM-8, which includes the aluminosilicate and substituted aluminosilicate zeolites described in U.S. Pat. No. 6,756,030 and the modified UZM-8 zeolites, such as, UZM-8HS which are described in U.S. Pat. No. 7,091,390. Each of U.S. Pat. No. 6,756,030 and U.S. Pat. No. 7,091,390 is herein incorporated by reference in its entirety.

The basic configuration of a catalytic aromatic alkylation zone is known in the art. The feed aromatic alkylation substrate and the feed olefin alkylating agent are preheated and charged to generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor 115 may contain one or more alkylation catalyst beds. Typically there are eight reactors in series in an alkylation zone. The invention encompasses dual zone aromatic alkylation processes such as those as described in U.S. Pat. No. 7,420,098 which is herein incorporated by reference in its entirety.

The particular conditions under which the alkylation reaction is conducted depends upon the aromatic compound and the olefin used. One condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. The alkylation conditions usually include a pressure in the range between about 1379 kPa(g) and 6985 kPa(g). The alkylation of the aromatic compounds with the olefins in the C2 to C20 range can be carried out at a temperature of about 60° C. to about 400° C. In a continuous process this space velocity can vary considerably, but is usually from about 0.1 to about 8 $hr^{-1}$ weight hourly space velocity (WHSV) with respect to the olefin. In particular, the alkylation of benzene with ethylene can be carried out at temperatures of about 150° C. to about 250° C. and the alkylation of benzene with propylene at a temperature of about 90° C. to about 200° C. The ratio of alkylatable aromatic compound to olefin used in the instant process will depend upon the degree of monoalkylation desired as well as the relative costs of the aromatic and olefinic components of the reaction mixture. For alkylation of benzene by propylene, the benzene-to-olefin molar ratio may be as low as about 0.1 and as high as about 10. Where benzene is alkylated with ethylene a benzene-to-olefin ratio may be between about 0.1 and 10.

The alkylation reaction zone will often provide a wide variety of secondary by-products. For example, in the alkylation of benzene with ethylene to produce ethylbenzene, the reaction zone can also produce di- and triethylbenzene in addition to other ethylene condensation products. Another non-limiting exemplary reaction that is contemplated herein includes the alkylation of benzene with propylene to produce cumene. In this type of reaction, the reaction zone can produce di- and triisopropylbenzene in addition to still more condensation products. As is well known in the art, these polyalkylated aromatics may contact additional aromatic substrate in a transalkylation zone to produce additional monoalkylated product. See e.g. U.S. Pat. No. 7,622,622 and U.S. Pat. No. 7,268,267, which are incorporated by reference herein. It should be noted that transalkylation reactions may occur in an alkylation reaction zone and alkylation reactions occur in a transalkylation reaction zone. Thus, as used herein alkylation zone 110 refers to a zone in which one or both of alkylation and transalkylation reactions occur. In an embodiment, the alkylated benzene product comprises at least one of ethylbenzene and cumene.

An alkylated aromatic separation zone may also be provided for separating a concentrated alkylated aromatic stream from the alkylated aromatic stream produced by the alkylation zone 110. The alkylated aromatic separation zone may include one or more distillation or fractionation columns or other separation apparatus as known in the art for separating a concentrated alkylated aromatic stream from other components in the alkylated aromatic stream. It should be noted that the term "concentrated" as used herein does not mean the resultant stream is free from other components, but rather that it has a higher concentration of the desired product than the stream fed into the separation apparatus. For example, as illustrated in FIG. 2, where the alkylation zone produces an ethylbenzene stream via line 135, the alkylated aromatic separation zone may include an ethylbenzene separation zone 150 for separating a concentrated ethylbenzene stream from a stream including benzene, poly-ethylbenzene, and other components. A benzene fractionation column 155 may be in fluid communication with an outlet of the alkylation zone 110 and configured to receive the ethylbenzene stream via line 135 from the alkylation zone outlet and to separate benzene from the feed stream, which exits the benzene fractionation column through an alkylation benzene recycle stream via line 160. The alkylation benzene recycle stream may be passed back to the alkylation zone 110 as additional benzene feed. An ethylbenzene fractionation column 165 may be in fluid communication with the benzene fractionation column 155 via line 170 and may be provided to receive the benzene reduced ethylbenzene stream via line 170 to produce a concentrated ethylbenzene stream via fractionation. The ethylbenzene may provide a product stream or it may be transferred downstream via line 175. A poly-ethylbenzene fractionation column 180 may be provided to receive the ethylbenzene depleted stream via line 185 and to separate a concentrated poly-ethylbenzene stream, which may be recycled back to a transalkylation reactor 120 via line 190 as a feed to the transalkylation reactor to produce additional ethylbenzene.

Figure 3:
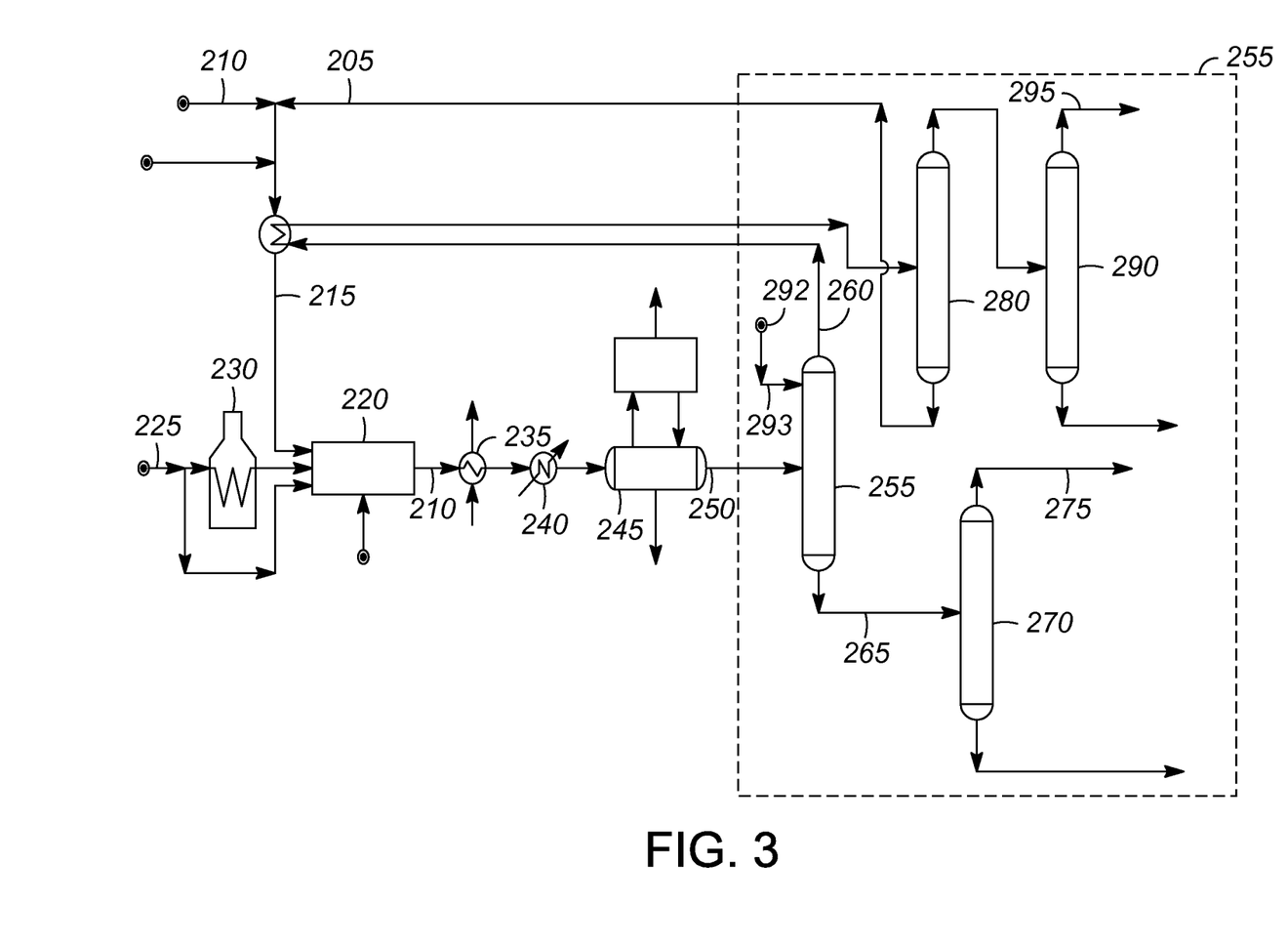
FIG. 3 is a flow diagram of a styrene monomer facility in accordance with various embodiments.

According to an aspect, the hydrocarbon stream may include a benzene recycle stream provided from a styrene monomer production zone. Turning to FIG. 3, an example of a styrene production zone 205 of a styrene production plant is illustrated. An ethylbenzene feed stream may be provided to the styrene monomer production zone 205 via line 210. The ethylbenzene feed stream may be provided via line 210 by forming the ethylbenzene stream by alkylation in the alkylation zone 110 and separation of the alkylation zone ethylbenzene stream by the separation zone 150 via line 175 to provide a concentrated ethylbenzene stream, which may include one or more other components, including benzene, as described above with regard to FIG. 2, or it may be provided by another source. In the styrene monomer production zone 205, the ethylbenzene stream is passed to a dehydrogenation zone 220 via line 215, where a dehydrogenation reaction occurs to produce a styrene stream via line 215.

The general layout and operation of styrene monomer production plants is well known, and one process flow is described and shown generally in U.S. Pat. No. 4,479,025, which is incorporated by reference herein. In an exemplary system, the dehydrogenation zone 220 includes one or more dehydrogenation reactors with a dehydrogenation catalyst for contacting the ethylbenzene stream and converting a portion of the ethylbenzene to styrene to form a mixed styrene stream, as is generally known in the art. The dehydrogenation zone 220 may also include steam sources and/or generators 225 and a superheater 230 for heating the steam, which is combined with the ethylbenzene feed stream and passed to the dehydrogenation zone 220. In the dehydrogenation zone 220, the ethylbenzene in the stream is contacted with the dehydrogenation catalyst under dehydrogenation conditions to produce a stream that includes unreacted ethylbenzene, styrene, benzene, steam, and hydrogen. The mixed styrene stream is cooled via heat exchanger 235 and sent to condenser 240 to produce a mixed phase stream. The stream is separated in the mixed phase separator into a liquid phase including water with dissolved hydrocarbons, a vapor phase, and a hydrocarbon liquid phase. The hydrocarbon liquid phase stream may include styrene, ethylbenzene, benzene, and other components, and is passed via line 250 to a separation zone 255.

As illustrated in FIG. 3, the separation zone may include an ethylbenzene/styrene splitter 255 for separating an ethylbenzene stream, including benzene and toluene, via line 260 from a styrene concentrated stream via line 265. The concentrated styrene stream may be passed via line 265 to a styrene finishing column 270 to produce a styrene product via line 275. The ethylbenzene stream may be passed via line 260 to an ethylbenzene recycle column 280. The ethylbenzene recycle column separates an ethylbenzene recycle stream and a stream including lighter hydrocarbon components, including benzene, which is passed via line 285 to benzene column 290. The benzene column 290 separates a benzene recycle stream that is exits the benzene column 290 via line 295.

According to one aspect, an inhibitor is added to the hydrocarbon liquid phase stream as is generally known in the art, in order to restrict the styrene from polymerizing and/or causing corrosion of the separation equipment. As described previously, the inhibitor may include one or more nitrogen compounds generally known to restrict polymerization of styrene and/or corrosion of equipment. Potential inhibitors are described above. As illustrated in FIG. 3, the inhibitor may be introduced from an inhibitor source 292 into the ethylbenzene/styrene splitter 255 via line 293.

Referring back to FIG. 2, the benzene recycle stream may be passed via line 300 back to the alkylation zone 110, via line 103 as shown in FIG. 2, where it is combined with the fresh benzene feed stream for treatment and subsequent alkylation of the combined benzene stream in the presence of ethylene to form additional ethylbenzene. Due to the introduction of the inhibitor and steam during the dehydrogenation and separation processes in the styrene monomer production zone 205 described previously with regard to FIG. 3, the recycle benzene stream will typically include water, one or more nitrogen containing compounds, and one or more unsaturated aliphatic compounds as described above and will have a different composition than the fresh benzene feed stream. In this regard, the benzene recycle stream may be passed via line 300 to the hydrocarbon treatment zone 4 described previously with regard to FIGS. 1 and 2, to remove at least a portion of these components prior to the benzene recycle stream entering the alkylation zone 110, where these components could potentially cause deactivation of the alkylation or transalkylation catalyst or otherwise shorten the life of the catalyst.

The exemplary ethylbenzene production plant and styrene monomer production plant illustrated in FIGS. 2 and 3 respectively are intended to illustrate one possible process flow, and are not intended to limit the scope of the invention which may be practiced in other process flows.

The above description and examples are intended to be illustrative of the invention without limiting its scope. While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention Example 1

An illustrative example of a clay adsorbent for removing unsaturated aliphatic compounds from a feed stream includes a commercially available F-24 acidic clay adsorbent available from Engelhard. The clay was dried at 225° C. under nitrogen for four hours prior to loading. A mixture of 0.3 wt % isoprene in benzene was passed over the clay in an isothermal plug flow reactor at a liquid hourly space velocity of 2.25 hr⁻¹. The reactor pressure was 500 psig and the reactor temperature was 190° C. Bromine index was used to assess conversion of the isoprene. The feed had a Bromine Index of 1,000 and the product typically had a Bromine Index below 5.

the F-24 clay before passing over the NiGuard-1. Both adsorbents were equilibrated with 600 ppm of water before nitrogen compounds were introduced in the manner described in Example 2 and the test was carried out as described in Example 2. The analysis of the effluent or product from the test of Example 3 is reported in Table 1 below.

TABLE 1

| Example | Adsorbent | Feed | Feed Rate (g/hr) | Temperature (° C.) | Breakthrough (hours) | Nitrogen Ads. @ Breakthrough | Nitrogen on NiGuard-1 |
|---|---|---|---|---|---|---|---|
| 2 | NiGuard-1 | 600 ppm Water 703 ppm Isoprene 52 ppm ACN + Benzene | 90 | 170 | 40.5 | 0.432% | 0.432 wt-% N |
| 3 | F-24 + NiGuard-1 | 600 ppm Water 703 ppm Isoprene 52 ppm ACN + Benzene | 90 | 170 | 65 | 0.694% | 0.545 wt-% N |

Figure 4:
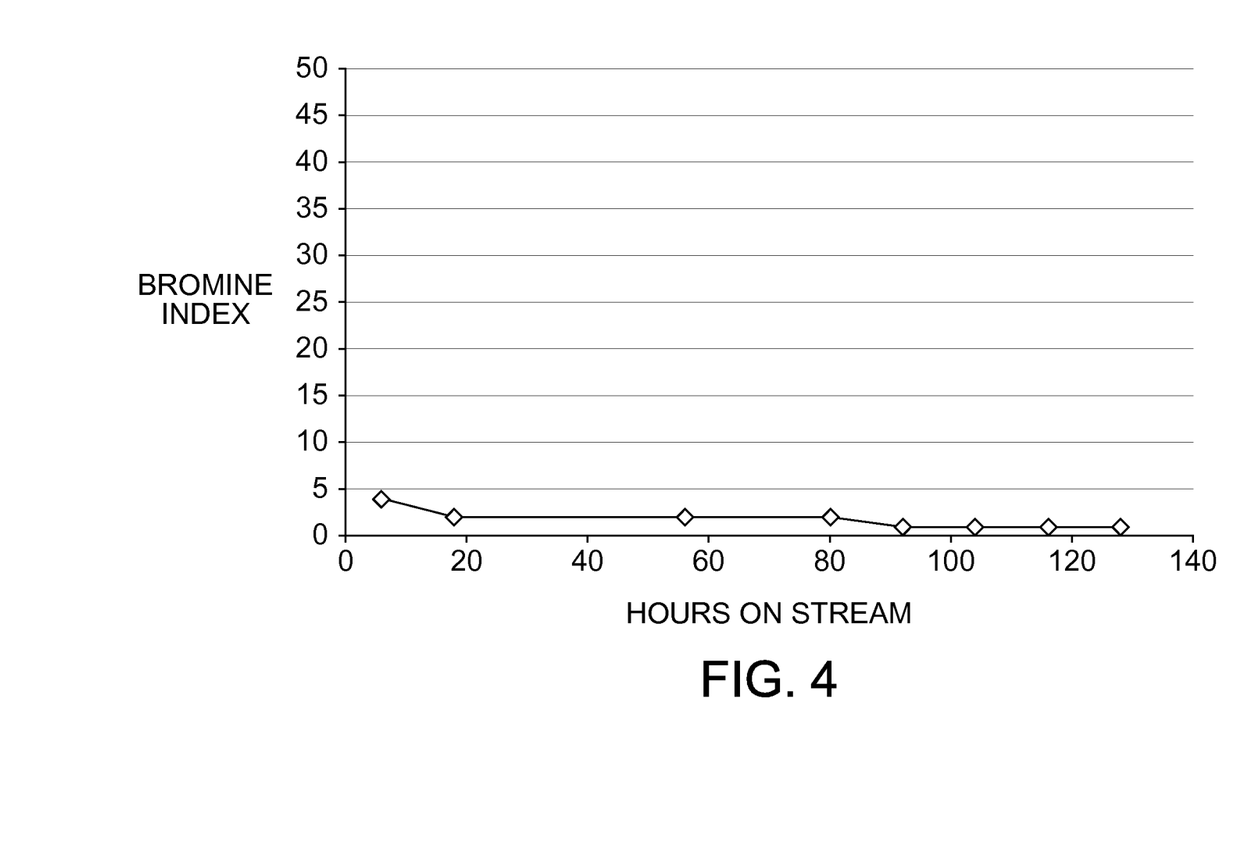
FIG. 4 is a graph showing in accordance with Example 1 showing Bromine Index on the y-axis and the Hours on Stream in the x-axis.

A benzene feed stream (>99 wt % benzene) containing 0.3 wt-% isoprene having a Bromine Index of 1,000 was used to evaluate the effectiveness of the F-24 clay adsorbent to remove the unsaturated aliphatic compounds as described below. The analysis of the benzene feed is illustrated in FIG. 4 which illustrates the analysis of the effluent or product from the test.

Example 2

As a comparative example, an acidic zeolitic adsorbent for removing nitrogen compounds from a feed stream included commercially available NiGuard-1 adsorbent. The NiGuard-1 adsorbent was dried at 287° C. under nitrogen for four hours to obtain an accurate weight. The adsorbent was loaded in to an isothermal plug flow reactor and pressured up to 550 psig with benzene and heated to 170° C. The adsorbent was equilibrated by passing 90 g/hr of benzene containing 600 ppm of water over it until the dew point analyzer on the reactor effluent stream read a constant amount of water in the reactor effluent. The reactor was kept at a constant temperature of 170° C. and pure benzene was flowed through the reactor at 90 g/hr to pressurize the system up to 550 psig. Once the system reached 550 psig, feed was introduced at 90 g/hr and the reactor effluent was analyzed via gas chromatography.

A simulated benzene recycle stream (>99 wt % benzene) containing different amounts of water, diolefins, and organic nitrogen components (600 wt-ppm water, 703 wt-ppm isoprene, and 52 ppm acetonitrile plus benzene) was used in the test. The nitrogen compound content was determined by gas chromatography. The analysis of the effluent or product from the test of Example 2 is reported in Table 1 below.

Example 3

As an illustrative example, a clay guard bed in accordance with Example 1 was positioned upstream of the NiGuard-1 adsorbent of Example 2. In an isothermal plug flow reactor, 27 cm³ of the F-24 clay was placed upstream of 27 cm³ of the NiGuard-1 adsorbent. The benzene stream was passed over The data demonstrate that positioning the clay adsorbent F-24 upstream of the NiGuard-1 adsorbent greatly increased the time until breakthrough from 40.5 hours to 65 hours. The nitrogen adsorption at breakthrough also increased from 0.432% to 0.694% when the F-24 clay bed was positioned upstream of the NiGuard-1 showing that nitrogen adsorption performance greatly improved overall when acidic clay adsorbent F-24 was positioned upstream of the NiGuard-1 zeolitic adsorbent.

The invention claimed is:

1. A process for treating one aromatic feed stream comprising an
   aromatic compound and an amount of nitrogen compounds comprising basic organic nitrogen compounds at a first concentration and another aromatic feed stream comprising the aromatic compound, an unsaturated aliphatic compound, water, and an amount of second nitrogen compounds comprising weakly basic nitrogen compounds at a second higher concentration, the method comprising:
   a) combining the other aromatic feed stream with the one aromatic feed stream to form a combined aromatic feed stream;
   b) contacting the combined aromatic feed stream of step (a) with an unsaturated aliphatic compound removal material comprising an acidic clay adsorbent to remove at least a portion of the unsaturated aliphatic compounds and reduce at least a portion of basic organic nitrogen compound from the combined aromatic feed stream to form a effluent stream;
   c) contacting the from step (b) with a nitrogen removal adsorbent comprising an acidic zeolite adsorbent to remove at least a portion of the nitrogen compounds from the combined aromatic feed stream to produce a treated aromatic feed stream; and
   d) contacting the treated combined aromatic feed stream from step (c) with an ethylene stream in the presence of an alkylation catalyst under alkylation conditions to form an ethylbenzene stream; wherein the aromatic compound comprises benzene and the other aromatic feed stream comprises a benzene recycle stream from a styrene monomer production zone.

2. The process of claim 1, wherein the one aromatic feed stream has a nitrogen compound concentration of between about 10 ppb-wt and 1 ppm-wt and the other aromatic feed stream has a nitrogen compound concentration of between about 1 ppm-wt and 10 ppm-wt.

3. The process of claim 1, wherein the other feed stream has an unsaturated aliphatic compound concentration of between about 10 ppm-wt and 1000 ppm-wt and the one feed stream has an unsaturated aliphatic compound concentration of below about 100 ppm-wt.

4. The process of claim 1, further comprising heating the combined aromatic feed stream to a contacting temperature of between about 45° C. and 250° C. before contacting the combined aromatic feed stream with the unsaturated aliphatic compound removal material.

5. The process of claim 1, further comprising introducing the treated combined aromatic feed stream into an aromatic compound separation column to form a treated feed stream with a higher concentration of the aromatic compound than the treated combined aromatic feed stream.

\* \* \* \* \*